US009845488B2

(12) United States Patent
Kirsch et al.

(10) Patent No.: US 9,845,488 B2
(45) Date of Patent: Dec. 19, 2017

(54) METHOD FOR THE DEPARAFFINISATION OF BIOLOGICAL SPECIMENS

(75) Inventors: Christoph Kirsch, Pulheim (DE); Claudia Beyard, Zuelpich (DE); Markus Meusel, Wuerselen (DE); Klaus Moeller, Eschweiler (DE)

(73) Assignee: Axagarius GmbH & Co. KG, Düren (DE)

( * ) Notice: Subject to any disclaimer, the term of this patent is extended or adjusted under 35 U.S.C. 154(b) by 1116 days.

(21) Appl. No.: 12/827,210

(22) Filed: Jun. 30, 2010

(65) Prior Publication Data

US 2011/0003369 A1 Jan. 6, 2011

(30) Foreign Application Priority Data

Jul. 1, 2009 (DE) ........................ 10 2009 031 434

(51) Int. Cl.
*C07H 1/08* (2006.01)
*C12Q 1/68* (2006.01)
*C12N 15/10* (2006.01)

(52) U.S. Cl.
CPC ....... *C12Q 1/6806* (2013.01); *C12N 15/1003* (2013.01)

(58) Field of Classification Search
CPC ................................................. C12N 15/1003
See application file for complete search history.

(56) References Cited

U.S. PATENT DOCUMENTS

| 5,346,994 | A | 9/1994 | Chomczynski |
| 7,544,471 | B2 | 6/2009 | Wang et al. |
| 2005/0014203 | A1 | 1/2005 | Darfler et al. |
| 2006/0252025 | A1* | 11/2006 | Nitta et al. ........................ 435/2 |
| 2007/0026432 | A1 | 2/2007 | Ke et al. |
| 2008/0220418 | A1 | 9/2008 | Ballhause et al. |
| 2009/0155907 | A1* | 6/2009 | Winther et al. ............... 435/378 |
| 2009/0202998 | A1 | 8/2009 | Schlumpberger et al. |

FOREIGN PATENT DOCUMENTS

| DE | 10 2005 060 738 A1 | 6/2007 |
| EP | 1743939 A2 | 1/2007 |
| WO | WO-1998/14460 A1 | 4/1998 |
| WO | 01/46402 A1 | 6/2001 |
| WO | WO-2002/23156 A1 | 3/2002 |
| WO | WO 2006/039563 * | 4/2006 |
| WO | 2006/130632 A2 | 12/2006 |
| WO | 2008/021419 A2 | 2/2008 |

OTHER PUBLICATIONS

Hi-Valley MSDS (accessed from http://www.hvchemical.com/msds/dlimo.htm on Sep. 26, 2012, 5 pages).*
Filipsson et al. (Concise international chemical assessment document 5, Limonene, dated 1998, accessed from http://whqlibdoc.who.int/publications/1998/9241530057.pdf on Sep. 26, 2012, 36 pages).*
Sigma-Aldrich (Materials Safety Data Sheet, accessed from http://www.sigmaaldrich.com/MSDS/MSDS/PleaseWaitMSDSPage.do?language=&country=US&brand=SIAL&productNumber=297879&PageToGoToURL=http://www.sigmaaldrich.com/catalog/product/sial/297879?lang=en&region=US on Sep. 26, 2012, 7 pages).*
Schewe et al, "Inter-laboratory validation of PCR-based detection of Mycobacterium tuberculosis in formalin-fixed, paraffin-embedded tissues", Virchows Arch, 2005, pp. 573-585, vol. 447, No. 3.
Sato et al, "Comparison of DNA Extraction Methods for Polymerase Chain Reaction Amplification from Formalin-Fixed and Paraffin-Embedded Tissues", Diagnostic Molecular Pathology, 2001, pp. 265-271, vol. 10, No. 4.
Lehmann et al, "Real-Time PCR Analysis of DNA and RNA Extracted from Formalin-Fixed and Paraffin-Embedded Biopsies", Methods, 2001, pp. 409-418, vol. 25, No. 4.
Banerjee et al, "Microwave-Based DNA Extraction from Paraffin-Embedded Tissue for PCR Amplification", Biotechniques, 1995, 4 pages, vol. 18, No. 5.
Guerrero et al., "Effects of Formalin Fixation and Prolonged Block Storage on Detection of Hepatitis C Virus RNA in Liver Tissue", Diagnostic Molecular Pathology, vol. 6(5), pp. 277-281 (1997).
BioGenex Laboratories Inc.: Safety data sheet EZ Dewax Solution, Ready to Use, 30. Oktober 2003 (Oct. 13, 2003), XP002599848, Gefunden im Internet: URL:http://www.biogenex.com/int msds/931-HK585-En-1232081898.pdf?Phpsessid=b382f56e2aa222aec2561f35b9c753e4 [gefunden am Sep. 8, 2010] * das ganze Dokument *.

* cited by examiner

*Primary Examiner* — Bin Shen
(74) *Attorney, Agent, or Firm* — Drinker Biddle & Reath LLP (57) ABSTRACT

A method for isolating biomolecules from a fixed biological specimen embedded in paraffin, comprises the steps of bringing the specimen into contact
a) with a solvent non-miscible with water and dissolving the paraffin in this solvent such as to form a liquid organic phase, and
b) with an aqueous solution of at least one lysis substance and/or with water and at least one lysis substance such as to form an aqueous phase;
isolation of the biomolecules from the aqueous phase. The invention further relates to a corresponding kit as well as to the use of such a kit for isolating biomolecules.

36 Claims, 4 Drawing Sheets

METHOD FOR THE DEPARAFFINISATION OF BIOLOGICAL SPECIMENS

CROSS-REFERENCE TO RELATED APPLICATIONS AND CLAIM TO PRIORITY

This application is related to application number 10 2009 031 434.2-52, filed Jul. 1, 2009, in the Federal Republic of Germany, the disclosure of which is incorporated herein by reference and to which priority is claimed.

FIELD OF THE INVENTION

The present invention relates to a method for isolating biomolecules from a fixed biological specimen embedded in paraffin, a kit which contains the substances required to carry out the method according to the invention, and the use of the kit according to the invention in order to carry out the isolation method.

BACKGROUND OF THE INVENTION

Methods for isolating biomolecules from fixed biological specimens embedded in paraffin are known from the prior art. Within this context a fixed specimen is to be understood as a biological specimen which is made sustainable in a way known in its own right by treating, for example, with a formaldehyde solution, anhydrous ethanol or acid alcoholic solutions. In order to further improve storage stability these specimens are then transferred into paraffin. The specimens treated with formalin and embedded in paraffin are also called FFPE ("formalin-fixed, paraffin-embedded") material. The specimens fixed and embedded using these methods can be used, for example, for histopathological examinations and/or then be kept over a very long period without any appreciable change taking place to the biomolecules contained within these specimens. In particular, even after long periods of time, the nucleic acids, i.e. RNA and DNA, can still be extracted from these specimens.

However, the extraction of these biomolecules from this type of fixed specimen embedded in paraffin is complex because the specimens must first of all be released from the paraffin surrounding them. The specimens are generally thin sections the paraffin portion of which generally considerably exceeds the specimen portion. Since the paraffin can interfere with or totally prevent further specimen preparation and isolation of the biomolecules, various methods are proposed in the prior art by means of which the paraffin can be separated out.

In WO 2006/039563 it is proposed to pre-treat the biological sample after cutting, for example with a microtome, with xylene, toluene, isoparaffin or limonene in order to dissipate the paraffin. This solution is then centrifuged, the solvent is removed, and the specimen optionally washed with ethanol in order to remove any solvent residues which may be present. Next the specimen is dried and then subjected to further analysis.

The multiple steps of washing with ethanol required in order to extract clean specimen material are on the one hand complex and, moreover, conceal the risk of parts of the specimen material inadvertently already being removed after centrifuging out when subtracting the ethanol supernatant. The same problem arises during the centrifugation and removal of the solvent for the paraffin. This is particularly problematical if only a small amount of specimen material is available because then the specimen material can hardly be identified by the naked eye in the solvent. Since the preparation of clean specimens using this method requires a great deal of skill, and above all experience, reliable automation is hardly possible.

In US 2007/0026432 a further method for the analysis of fixed biological specimens embedded in paraffin is described. For this purpose it is proposed to heat the specimen material embedded in paraffin to above the fusion point of the paraffin after adding detergents, and then to allow the specimen to cool down again to below the fusion point of the paraffin. Extraction of the specimen material is then implemented with the aid of a cannula which is moved through the solidified paraffin layer into the specimen material located beneath the latter. It is a disadvantage with this method that when penetrating the paraffin layer the cannula can become blocked with paraffin, and this makes automation practically impossible.

SUMMARY OF THE INVENTION

It is the object of the present invention to provide a method for the isolation of biomolecules from a fixed biological specimen embedded in paraffin which makes it possible to extract the greatest possible quantity of biomolecules from the specimen, prevents losses, as may arise by removing an organic phase with the paraffin dissolved within the latter, and which furthermore is suitable for automated specimen preparation.

This object is achieved according to the invention by a method for isolating biomolecules from a fixed biological specimen embedded in paraffin which comprises the following steps:

Bringing the specimen into contact a) with a solvent not miscible with water and dissolving the paraffin in this solvent such as to form a liquid organic phase, and b) with an aqueous solution of at least one lysis substance and/or with water and at least one lysis substance such as to form an aqueous phase;

isolation of the biomolecules from the aqueous phase.

The knowledge underlying the present invention is that in order to isolate biomolecules from a biological specimen embedded in paraffin, in order to dissipate the paraffin said specimen can be displaced with a solvent not miscible with water which together with the paraffin forms an organic phase which can remain in the specimen receptacle during the further preparation of the specimen. The requirement for removal of the solvent is therefore just as small as that for the implementation of successive washing steps, and in this way the complexity of the method can be considerably reduced. By dispensing with the multiple washing steps provided in the prior art when using solvents, the risk of loss of specimen material is excluded as far as possible.

DETAILED DESCRIPTION OF THE PREFERRED EMBODIMENT(S)

The method according to the invention further ensures that the organic phase comprising paraffin and solvent non-miscible with water is liquid at normal ambient temperatures. When extracting the specimen by means of the organic phase, such as for example using a cannula or pipette moved through the latter, blocking with paraffin can therefore be ruled out. The method according to the invention can therefore also be implemented in an automated manner using appropriate pipetting robots. The fact that the method according to the invention can also be implemented without any centrifugation steps additionally facilitates automation. In particular, at a temperature of ≤25° C., preferably ≤20° C. or ≤15° C., the organic phase is liquid.

With the aid of the method according to the invention in principle all types of biomolecule can be isolated from biological specimens. These are for example nucleic acids and/or proteins. RNA and DNA with different chain lengths, in particular with more than fifteen nucleotides, such as for example single- and double-stranded bacterial, viral, human, animal or plant RNA or DNA, in particular genomic DNA, mitochondrial DNA, plasmids, mRNA, tRNA, rRNA, miRNA and other short RNA species, in particular with a chain length of 15 to 25 nucleotides, can be considered as nucleic acids. All previously specified biomolecules can be isolated individually or also in any combination by the method according to the invention. The specimens are present for example in the form of thin sections of the biological specimen embedded in paraffin, as obtained by means of a microtome.

A solvent non-miscible with water is understood as being a solvent which at 25° C., with a mix ratio of 1:1 with water, forms two phases separated from one another. The solvents used within the framework of the present invention should advantageously, moreover, have good dissolution properties in relation to the paraffins normally used for the embedding of biological specimens. For this purpose, in order to dissolve 1 mg paraffin at 25° C., a quantity of solvent of no more than 500 µl should be required, preferably no more than 300 µl, particularly preferably no more than 150 µl.

Within the context of the present invention a lysis substance is understood as being a compound which is capable of releasing biomolecules from the material of the biological specimen. These can be one or more enzymes, for example proteases.

One or more chaotropic salts can also be used as lysis substances. For this purpose guanidinium salts such as guanidinium thiocyanate or guanidinium hydrochloride, sodium or potassium thiocyanate, potassium iodide, perchlorates or barium salts are especially considered.

Other substances supporting the lysis can also be used within the context of the invention.

The aforementioned lysis substances, i.e. e.g. enzymes and chaotropic salts, can be used alternatively or in any combinations. Provision is made according to the invention such that the lysis substance is already present in the form of an aqueous solution, or by adding water and a lysis substance, an aqueous solution is formed in situ. In both cases therefore an aqueous phase is formed.

If within the framework of the method according to the invention both enzymes and chaotropic salts are used, it is advantageous if first of all the enzyme or enzymes are added as well as, if so desired, a small quantity of chaotropic salt, and is then incubated. In a second step the chaotropic concentration can then be increased to the desired level or, if initially only enzymes are added, in this step the whole quantity of chaotropic salt is added. This applies to the case where aqueous solutions of these substances are used and in the case of the use of water and solid lysis substances. In this way a possible reduction in the activity of the enzyme or enzymes can be prevented by an excessively high initial concentration of chaotropic salt.

With biological specimens which have been fixed by means of a formalin solution, in step b) a lysis substance should advantageously be used which supports the removal of cross-linkings brought about by the formalin treatment, such as for example enzymes, in particular a protease. With biological specimens fixed with ethanol or acid alcoholic solutions the addition of a chaotropic salt in procedural step b) may suffice in order to release the biomolecules contained in the biological specimen.

Within the framework of the method according to the invention it is possible for step a) to be implemented before, after or at the same time as step b). Advantageously, however, step a) is implemented before step b) since in this way the paraffin can be removed from the biological specimen before one proceeds with the lysis of the specimen in step b).

In one embodiment of the method according to the invention the solvent non-miscible with water has a lesser density than water and/or the aqueous solution. The density of the solvent non-miscible with water is in particular ≤0.95 g/cm$^3$ or ≤0.90 g/cm$^3$. With the addition of this type of solvent to the biological specimen embedded in paraffin the latter forms a supernatant as an organic phase after subsequently adding the water or the aqueous lysis solution. Since the biological specimen generally has a density which is either equal to or greater than that of water, the specimen material is in the aqueous phase, by means of which the lysation of the specimen is accelerated by a better effect of the lysis substance contained in the aqueous phase and runs off totally. For this purpose the mixture can also be agitated if the specimen initially floats on the liquid surface due to the surface tension. Moreover, the biological specimens are generally hydrophilic, and so can easily be hydrated, and this also facilitates the cross-over from the organic phase into the aqueous phase. This also applies in the case where the solvent non-miscible with water has a higher density than water or the aqueous solution.

At the same time the supernatant formed by the organic phase protects the specimen against the effect of atmospheric oxygen which can lead to an oxidative change in the biomolecules to be isolated. Since the specimen receptacles generally taper off in the ground region, easier removal of the aqueous phase is moreover possible.

The isolation of the biomolecules from the aqueous phase can take place in a way known in its own right. For this purpose the biomolecules to be isolated are bonded, for example, to a solid carrier. Silica membranes or loose silica particles, polymer, glass particles or magnetic beads can be used for this. For this step the aqueous phase can either be removed from the specimen receptacle and brought onto the solid phase, for which purpose other suitable binding conditions can optionally be set. This is achieved, for example, by adding a chaotropic salt and/or one or more alcohols with one to four carbon atoms, such as in particular methanol or ethanol, to the aqueous phase. The binding conditions can preferably be set in the presence of the organic phase.

Alternatively to this, the solid carrier, for example in the form of magnetic beads, can be added to the two-phase mixture of organic and hydrous phase, in this case too it being possible to improve the binding conditions dependently upon the surface properties of the beads, e.g. by adding chaotropic salts and/or the aforementioned alcohols. The biomolecules then bind in the two-phase mixture to the solid carrier and can then be separated off.

The isolation of the biomolecules from the aqueous phase is not necessarily dependent, however, upon the presence of a solid phase. Nucleic acids can, for example, be precipitated or extracted from the aqueous phase using known methods.

In a further embodiment of the method according to the invention the solvent non-miscible with water is liquid at ≤25° C., in particular at ≤20° C., preferably at a temperature of ≤15° C., particularly preferably at ≤10° C. In this way it can be ensured that the organic phase also remains in liquid form at cooler ambient temperatures, even after dissolving the paraffin.

In a further development of the method according to the invention the solvent non-miscible with water is selected from aromatic hydrocarbon compounds with 6 to 30 carbon atoms, aliphatic hydrocarbon compounds with 10 to 30 carbon atoms, comprising in particular alkanes or alkenes. Particularly suitable are linear hydrocarbon compounds with 9 to 15 carbon atoms, in particular with 12 to 15 carbon atoms or mixtures of the latter. In particular the aforementioned linear hydrocarbon compounds are saturated or simply unsaturated. These are for example n-nonane, n-decane, n-undecane, n-dodecane, n-tridecane and particularly preferably n-tetradecane, n-pentadecane and n-pentadecene. But technical solvents such as biodiesel, diesel and heating oil, low viscosity paraffin, white oil, petroleum, kerosine or sinarol can also be used. Sinarol is a $C_{14}$-$C_{19}$ hydrocarbon mixture with a boiling range of 250° C.-330° C.

Moreover, alkanoic or alkenoic acids with 2 to 20, in particular 6 to 18 carbon atoms and derivatives of the latter, aromatic or aliphatic alcohols with 6 to 12 carbon atoms can be used. Mixtures of all of the aforementioned substances are also possible. Examples of usable alkanoic acids are octane, nonane or decane acid.

The aliphatic hydrocarbon compounds can be linear, branched, cyclic, saturated or unsaturated or be made up of mixtures of the latter. If aromatic hydrocarbon compounds with aliphatic substituents are used, the latter can also be linear, branched, cyclic, saturated or unsaturated. Examples of usable cyclic or aromatic hydrocarbons are pinene and limonene on the one hand, and xylene and cymene on the other hand.

It is also possible for the aromatic and/or aliphatic hydrocarbon compounds to carry heteroatoms, such as for example groups containing sulphur, nitrogen, oxygen, fluorine, chlorine, bromine and/or iodine.

Preferred alkanoic or alkenoic acid derivatives are esters of the latter, in particular alkyl esters of the latter comprising linear carboxylic acids and linear alcohols having respectively one to 14 carbon atoms, the ester having in particular 5 to 20 carbon atoms. These are for example acetic acid butyl ester, propionic acid ethyl ester, propionic acid pentyl ester, propionic acid octyl ester, propionic acid decyl ester, butylic acid decyl ester, pentylic acid octyl ester, octylic acid hexyl ester, octylic acid octyl ester, decylic acid butyl ester and dodecylic acid butyl ester.

Furthermore, saturated and/or branched organic acid esters, such as for example octylic acid isoamyl ester or also esters of multivalent organic acids, such as acetyl tributyl citrate, adipinic acid diethylester or malonic acid diethyl ester can also be used.

In order to improve a clear phase separation between organic phase and aqueous phase it is advantageous if the organic solvents used have a $K_{OW}$ value (n-octanol water distribution coefficient) of >1.0, in particular of ≥2.0. Particularly preferred are solvents with a $K_{OW}$ value of ≥4.0, in particular of ≥5.0 or of ≥6.0. When using these solvents a clear separation between organic phase and aqueous phase is achieved, even with increased temperatures or with the addition of chaotropic salt or alcohols such as ethanol or methanol, by means of which biomolecules can as far as possible be prevented from being displaced into the organic phase. Solvents with a $K_{OW}$ value of ≥5.0 are for example n-nonane, n-decane, n-undecane, n-dodecane, n-tridecane, n-tetradecane, n-pentadecane and the corresponding alkenes, in particular n-pentadecene.

In addition to the lysis substance and the chaotropic salt further substances can be added to the aqueous phase, such as for example at least one buffer substance and/or at least one alcohol with 1 to 4 carbon atoms and/or at least one reducing agent and/or buffer and/or reagent in order to eliminate any covalent combinations/modifications of the biomolecules caused by formalin treatment, such as ammonium chloride and/or alkyl amines.

Appropriate buffer substances are for example tris/HCl, phosphate buffer, borate buffer, PBS buffer, citrate buffer, MES buffer or HEPES buffer. Alcohols with 1 to 4 carbon atoms are for example methanol, ethanol, n/iso-propanol, butanols and mixtures of these alcohols. DTT, beta-mercaptoethanol, TCEF or other reducing agents can be used as reducing agents.

In a further embodiment of the method according to the invention the paraffin is dissolved by heating, in particular by heating to a temperature of 35 to 70° C., preferably to 40 to 60° C. By heating, more rapid dissolution of the paraffin in the solvent non-miscible with water is promoted, it being possible to largely rule out a thermal change to the specimen material by the moderate temperatures. Moreover, this heating with at the same time use of a lysis substance contributes to dissipating the cross-linkings in formalin-fixed biological specimens.

In a further development of the method according to the invention procedural step b) is implemented by heating, in particular to a temperature of 70 to 100° C. The heating in this step can be undertaken before, during and after adding the aqueous lysis substance solution or the water and the lysis substance. By heating the lysis of the specimen can be accelerated or proceed to a more complete extent, by means of which the biomolecules to be isolated are released more quickly or in the greatest possible quantity from the biological specimen.

When choosing the solvent non-miscible with water it is advantageous if the latter has a boiling point under normal pressure of at least 150° C., in particular at least 160° C. In this way the organic solvent added is prevented from evaporating too strongly during the process, in particular during heating, and the paraffin is prevented from being allowed back again undissolved. Moreover, evaporating the organic solvent can give rise to an odour nuisance or a negative impact upon health. Furthermore, solvent vapours are often also easily inflammable. By choosing a solvent with a relatively high boiling point the gaseous release of the latter at a given temperature is reduced, and this reduces the risk of fire. The low vapour pressure of these solvents also makes it possible to seal the specimen receptacle meanwhile without there being any risk of the latter cracking during heating.

In order to further improve handling safety, solvents non-miscible with water are used which have a flash point of at least 40° C., in particular of at least 50° C., preferably of at least 60° C., even more preferably of at least 70° C. or at the very least 80° C. These are, for example, acetyl tributyl citrate, adipinic acid diethyl ester, decanol, malonic acid diethylester, benzyl alcohol or mixtures of the latter. Preferred, moreover, are n-dodecane, n-tetradecane, n-pentadecane, n-pentadecene, biodiesel, sinarol or mixtures of the latter which are additionally characterised by particularly good phase separation characteristics to the aqueous phase.

The biomolecules can be isolated from the aqueous phase for example by adding the biomolecules to a solid phase, if so desired followed by one or more washing steps. Organic polymer particles and/or mineral carrier materials such as quartz fibres, silica gel, glass, aluminium oxide, zeoliths, titanium dioxide and/or zircon dioxide, for example, can be considered as a solid phase. These carriers can be present in particulate form, especially as magnetic and/or magnetisable particles, in particular magnetic beads. Furthermore, the carrier can be used as fibres, sponges, foams, in particular in the form of frits or membranes. Preferably, the solid phase is in the form of a chromatographic column. Here the solid phase can constitute the column packing and/or a membrane, for which purpose in particular the aforementioned organic polymer particles and/or mineral carrier materials can be used.

As a washing solution for the aforementioned washing steps high salt buffers and/or high alcohol can, for example, be used. High alcohol is understood as being alcohol/water mixtures with a high alcohol content of for example 70 or 80% by volume. Methanol, ethanol, n-/iso-propanol, butanols and mixtures of these alcohols, for example, can be considered as alcohols. The high alcohols can, moreover, contain small quantities of buffer substances.

The addition of the biomolecules to the solid phase can be achieved by the aqueous phase being brought fully and the organic phase being brought at least partially in contact with the solid phase. If silica materials are used as the solid phase, in order to improve the binding conditions, the aqueous phase can previously also be displaced with a chaotropic salt and/or an alcohol with one to four carbon atoms, such as for example methanol or ethanol. By using an organic solvent with a density less than that of water, one can proceed here such that the aqueous phase located beneath the organic phase in a specimen receptacle tapering on the floor side is extracted by a cannula or pipette guided directly over the floor until part of the supernatant organic phase is also carried over. Therefore, the most complete possible conveyance of the biomolecules out of the specimen receptacle can be achieved. The volume sucked out in this way can then be passed to a chromatographic column in order to bind the biomolecules to the solid carrier. Contaminations, which also bind to the solid carrier under these conditions, can, if so desired, be totally removed by one or more washing steps. For this purpose high salt buffers and/or high alcohol or also other solutions known to the person skilled in the art for these purposes can be used.

When using magnetic or magnetisable particles, in particular magnetic beads, the latter can also be passed directly to the two-phase system comprising the organic and the aqueous phase, and the aqueous phase with the particles can then be separated out. If the organic phase has a greater density than the aqueous phase, in this step the particles are separated out with the organic phase. With the addition of the particles, in order to improve the binding conditions the aqueous phase can previously also be displaced with a chaotropic salt and/or an alcohol with one to four carbon atoms and/or the separation out of the charged particles can be supported by centrifugation.

According to a further embodiment of the method according to the invention the aqueous and/or organic phase is free as far as possible from tensides, in particular from anionic, cationic and/or amphoteric tensides. In this way a clear phase separation between the aqueous and organic phase can be guaranteed.

Further subject matter of the present invention relates to a kit for isolating biomolecules from a fixed biological specimen embedded in paraffin, in particular a tissue specimen which contains at least the following components:
a) a solvent non-miscible with water, and
b) at least one lysis substance and/or an aqueous solution of at least one lysis substance.

In this kit the specified components are preferably to be found in different containers. If the lysis substance is already present as an aqueous solution, when using the kit one can dispense with the further addition of water.

In an advantageous embodiment of the kit according to the invention the latter contains method instructions in which the implementation of the method according to the invention is printed out. This guarantees the most error-free possible usage of the kit according to the invention.

Moreover, the present invention relates to the use of a kit according to the invention for isolating biomolecules from a fixed biological specimen embedded in paraffin.

In the following the method according to the invention is described in greater detail by means of exemplary embodiments.

EXAMPLE 1

Isolation of RNA from Rat Liver FFPE Specimens

In order to compare the method according to the invention with the method known from the prior art using xylene in order to remove the paraffin, specimen sections with the same thickness of approximately 7.5 µm of rat liver FFPE specimens are subjected to the corresponding method protocols. As a solid phase for the isolation of nucleic acids commercially available binding columns with silica membrane are used (NucleoSpin RNAXS, MACHEREY-NAGEL, Düren). These columns can be inserted into appropriate collecting tubes and easily be processed in any commercially available centrifuge.

| Protocol: Final paraffinisation with xylene (prior art) |
|---|
| 1-3 FFPE sections, 7.5 µm thick, per preparation |
| Addition of 1 ml xylene |
| Incubation for 2 mins at room temperature, 25° C. (RT), vortex for 10 secs. |
| Centrifugation max. speed 2 mins (approx. 14,000 x g) |
| Pippette off and discard supernatant |
| Addition of 1 ml ethanol (~98%) |
| Vortex for 2 secs. |
| Centrifugation max. speed 2 mins |
| Pipette off and discard supernatant |
| Dry at 60° C. for 3-10 mins with open lid (or longer until ethanol is fully evaporated) |
| Addition of 100 µl lysis buffer (3M GITC, 10 mM Tris, pH 7.0) |
| Addition of 10 µl proteinase K (20 mg/ml) |
| Vortex for 10 secs. |
| Centrifuge for a short time |
| If specimen residues remain on the wall of the receptacle, the latter are carefully flushed back into the solution. |
| Pipetting up and off of the solution for homogenisation. |
| Proteinase K digestion at 60° C. for 15 mins. Remove receptacle from the incubator and vortex for 5 secs. If tissue residues are still visible, incubation should be continued for up to 3 hrs. |
| Addition of 100 µl 200 mM ammonium chloride |
| Vortex |
| Incubation at 90° C. for 15 mins. Allow to cool down to RT for approx. 2 mins. |
| Addition of 200 µl ethanol (96-100%) |
| Mix |
| Centrifuge for a short time (approx. 1 sec 1000xg) |
| Pipette up and off the mixture 3x and pass the specimen (410 µl) to the NucleoSpin RNA XS binding column and continue with standard protocol (see below). |

| Protocol: Deparaffinisation according to the invention |
| --- |
| 1-3 FFPE sections, 7.5 µm thick, per preparation |
| Addition of 0.3 ml pentadecane |
| Incubation for 2 mins at 60° C. and then immediately vortex (in order to fuse and dissolve paraffin) |
| Allow to cool down to room temperature (5 mins) |
| Addition of 100 µl lysis buffer (3M GITC, 10 mM Tris, pH 7.0) |
| Vortex in order to transfer the tissue from the upper organic into the lower aqueous phase |
| Centrifugation for 1 min with max. g-number in order to support the phase separation and the cross-over of the tissue into the aqueous phase. |
| Addition of 10 µl proteinase K (20 mg/ml) to the aqueous phase. Mixing of the aqueous phase by pipetting up and off. Do not mix the aqueous with the organic phase. |
| Proteinase digestion at 60° C. for 15 mins. Remove receptacle from the incubator and vortex for 5 secs. If tissue residues are still visible the incubation should be continued for up to 3 hrs. |
| Addition of 100 µl 200 mM ammonium chloride to the aqueous phase |
| Vortex in order to mix the ammonium chloride with the aqueous phase. Optionally, short centrifugation in order to support the phase separation. |
| Incubation at 90° C. for 15 mins. Allow to cool down to RT for approx. 2 mins. |
| Addition of 200 µl ethanol (96-100%) |
| Mix |
| Centrifuge for a short time (approx. 1 sec 1000xg) |
| Pipette mixture up and off 3x and pass the specimens (410 µl) to the NucleoSpin RNA XS binding column and continue with RNA isolation protocol (see below). Residues of the organic phase which are optionally also transferred are uncritical. |

| | RNA isolation protocol after deparaffinisation with xylene and deparaffinisation according to the invention |
| --- | --- |
| 1 | Loading of the spin columns and centrifugation at 8,000xg for 30 secs |
| 2 | Discarding of the collecting tube with the throughput |
| 3 | Place spin column in new collecting tube (2.0 ml) |
| 4 | Addition of 100 µl 75% ethanol |
| 5 | Centrifugation at 11,000xg for 30 secs |
| 6 | Addition of 25 µl Dnase |
| 7 | Incubation at 20-25° C. for 15 mins |
| 8 | Addition of 100 µl 2 M GITC, 10 mM Tris, pH 7.0, 75% ethanol |
| 9 | Incubation at 20-25° C. for 2 mins |
| 10 | Centrifugation at 11,000xg for 30 secs |
| 11 | Addition of 400 µl 75% ethanol |
| 12 | Centrifugation at 11,000xg for 30 secs |
| 13 | Discarding of the collecting tube with the throughput |
| 14 | Place spin column in new collecting tube (2.0 ml) |
| 15 | Addition of 200 µl 75% ethanol |
| 16 | Centrifugation at 1,000xg for 2 mins |
| 17 | Discarding of the collecting tube with the throughput |
| 18 | Place spin column in new collecting tube (1.5 ml) |
| 19 | Addition of 10 µl RNase-free water |
| 20 | Centrifugation at 11,000xg for 30 secs. Collection of the eluate in the collecting tube and storage of the extracted RNA at −20 or −70° C. |

The isolated RNA was quantified by means of qRT-PCR as follows:

Target: HPRT (hypoxanthineguanine phosphoribosyltransferase)
Amplicon size: 101 bp
Specificity: Rat, mRNA and cDNA
PCR equipment: LightCycler
Kit: Sigma SYBR Green Quantitative RT-PCR kit (#QR0100)
Template quantity: 2 µl The following components are mixed for each reaction batch:

| | |
| --- | --- |
| Water | 3 µl |
| SYBR Green Taq Ready Mix for QRT-PCR (from the kit: Sigma SYBR Green Quantitative RT-PCR kit (#QR0100)) | 10 µl |
| 1:20 diluted DuraScript RT (from afore-mentioned kit) | 1 µl |
| Primer A (10 µM = 10 pmol/µl) 5'-GCAGACTTTGCTTTCCTTGGT-3' | 2 µl |
| Primer B (10 µM = 10 pmol/µl) 5'-CTGGCCTGTATCCAACACTTC-3' | 2 µl |
| RNA eluate | 2 µl |
| Total volume | 20 µl |

The reaction batch is conveyed into a LightCycler capillary tube (produced by Roche). The reaction and analysis are carried out in the LightCycler instrument (produced by Roche) with the following programme:

| | Target Temp (° C.) | Incubation Time (sec) | Temperature Transition Rate (° C./sec) |
| --- | --- | --- | --- |
| Denaturation | 48 | 1800 | 20 |
| Denaturation | 94 | 30 | 20 |
| Amplification (40 cycles) | 94 | 5 | 20 |
| | 58 | 1 | 20 |
| | 72 | 2 | 20 |
| | 81 | 3 | 20 |
| Fusion curve | 95 | 0 | 20 |
| | 65 | 10 | 20 |
| | 95 | 0 | 0.1 |
| Cooling | 40 | 30 | 20 |

Figure 1:
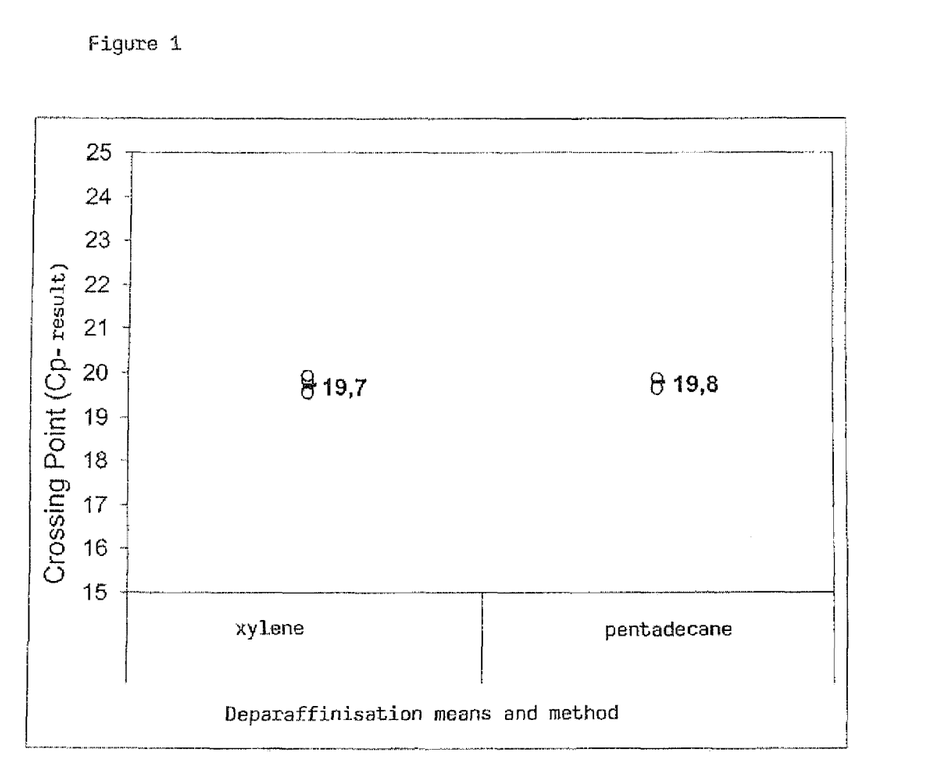
FIG. 1 illustrates the results of a measurement according to Example 1.

In FIG. 1 the result from the measurement is shown. The Cp values obtained, which constitute a measure for the quantity of RNA obtained, show the same results for both methods. Therefore, the RNA yield for the method according to the invention corresponds as far as possible to the quantity obtained by means of the substantially more complex xylene deparaffinisation pretreated specimen.

EXAMPLE 2

RNA and DNA Isolation from Rat Liver FFPE Specimens

With this experiment, in addition to RNA, DNA is also isolated from the specimens, the protocols described in Example 1 for deparaffinisation by means of a xylene method and the method according to the invention remaining unchanged. With regard to the extraction of nucleic acid, in Example 2 the DNase digestion is dispensed with, and instead of this selective elution of the genomic DNA is undertaken.

| Protocol: DNA and RNA isolation |
| --- |
| Deparaffinisation with xylene and using the method according to the invention in Exemplary Embodiment 1. |
| Loading of the binding column, centrifugation and discarding of the collecting tube with the throughput. |
| Placing of the binding column with the associated RNA and DNA into a new collecting tube (2.0 ml). Unlike Exemplary Embodiment 1, one proceeds as follows for the elution of the DNA: |
| DNA steps: Addition of 100 µl 10 mM $CaCl_2$, 80% ethanol, 10 mM Tris, pH 7.0 to the binding column |
| Centrifugation at 11,000 x g for 30 secs |
| With this step it is not necessary to exchange the collecting tube after the centrifugation. |
| New addition of 100 µl 10 mM $CaCl_2$, 80% ethanol, 10 mM Tris, pH 7.0 to the binding column |
| Centrifugation at 11,000 x g for 2 mins |
| Discarding of the collecting tube with the throughput |
| Placing of the binding column into a new collecting tube (1.5 ml) |
| Addition of 10 µl 10 mM $CaCl_2$, 10 mM Tris, pH 7.0 directly to the centre of the silica membrane of the binding column |
| Centrifugation at 11,000 x g for 30 secs |
| Storage of the eluted DNA for later analysis. |
| Placing of the binding column into a new collecting tube (2.0 ml) |
| From here one continues with step 6 of the RNA isolation protocol according to Example 1. |

The analysis of the isolated DNA takes place by means of qPCR which has been implemented as follows:

Target: GAPDH

Amplicon size: 191 bp

Specificity: Mouse, gDNA

PCR equipment: LightCycler

Kit: DyNamo Cypillary SYBR Green Kit (Finnzymes #F-420S/L)

Template quantity: 2 µl

In order to analyse the DNA eluates a qPCR is carried out as follows.

The following components are mixed for each reaction batch:

```
2x DyNAmo master mix (from kit: DyNAmo      10 µl
Capillary SYBR Green qPCR kit #F-
4205/L)

Primer A (10 µM = 10 pmol/µl)               0.5 µl
5'-AACGACCCCTTCATTGAC-3'

Primer B (10 µM = 10 pmol/µl)               0.5 µl
5'-TCCACGACATACTCAGCAC-3'

Water                                       7 µl

DNA eluate                                  2 µl

Total volume                                20 µl
```

The reaction batch is conveyed into a LightCycler capillary tube (produced by Roche). The reaction and analysis are carried out in the LightCycler instrument (produced by Roche) with the following programme.

| | Target Temp (° C.) | Incubation Time (sec) | Temperature Transition Rate (° C./sec) |
| --- | --- | --- | --- |
| Denaturation | 95 | 600 | 20 |
| Amplification (40 cycles) | 95 | 5 | 20 |
| | 55 | 10 | 20 |
| | 72 | 12 | 20 |
| Fusion curve | 95 | 10 | 20 |
| | 65 | 20 | 20 |
| | 95 | 0 | 0.2 |
| Cooling | 40 | 30 | 20 |

The analysis of the isolated RNA takes place by means of qRT-PCR, as described in Example 1.

Figure 2:
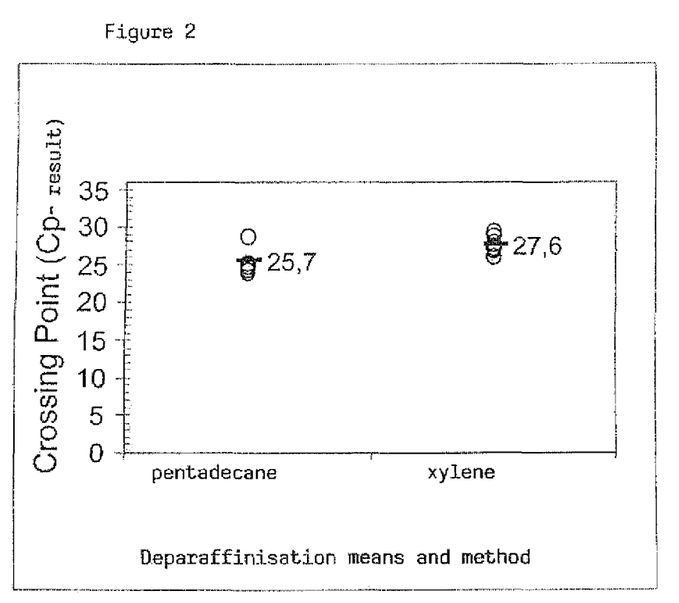
FIG. 2 illustrates the results of a DNA analysis according to Example 2.
Figure 3:
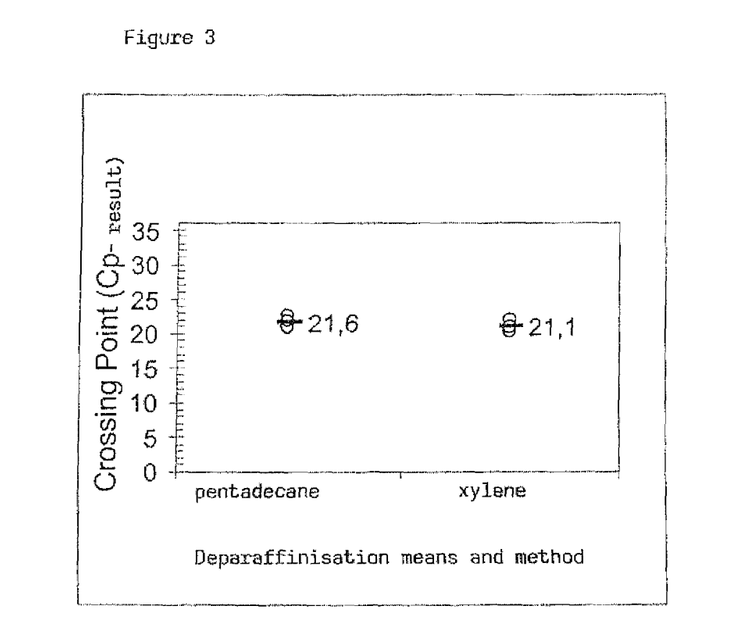
FIG. 3 illustrates the results of an RNA analysis according to Example 2.

In FIG. 2 the results of the DNA analysis, and in FIG. 3 the results of the RNA analysis are shown. These make it clear that with the aid of the isolating method according to the invention DNA can also be isolated in addition to RNA from FFPE specimens in quantities which are comparable to those of the xylene deparaffinisation method. Therefore, the method according to the invention achieves the performance of the specimen preparation by means of the xylene method while avoiding the disadvantages associated with this method.

EXAMPLE 3

RNA Isolation from Rat Liver FFPE Specimens by Means of Biodiesel or Sinarol as Solvents Non-Miscible with Water The FFPE specimens are treated as described in Exemplary Embodiment 1, the deparaffinisation according to the method of the invention having been carried out with two different solvents, namely biodiesel and sinarol. Biodiesel (CAS No. 67762-38-3) is a mixture of different fatty acid methyl esters. The analysis of the isolated RNA took place by means of qRT-PCR, as described in Example 1.

Figure 4:
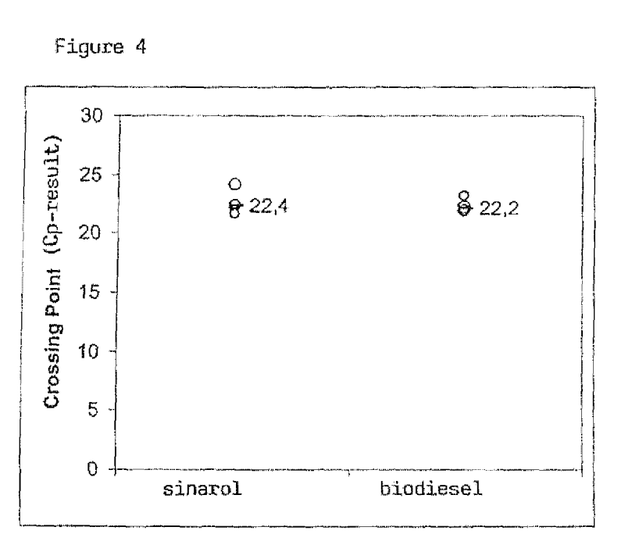
FIG. 4 illustrates the results of a comparison of solvents according to Example 1.

In FIG. 4 the result of the comparison of these two solvents, which in relation to the yield of isolated RNA give as far as possible the same results, is shown.

EXAMPLE 4

RNA Isolation from Rat Liver FFPE Specimens with Pentadecane and Low Viscosity Paraffin as a Comparison In this experiment the deparaffinisation by means of pentadecane and low viscosity paraffin (CAS No. 8012-95-1) according to the method of the invention are contrasted. For this purpose rat liver FFPE specimens as described in Example 1 were treated with pentadecane and low viscosity paraffin as solvents non-miscible with water, and the RNA was isolated from the specimens.

As a result it is shown how with both solvents the specimen can be deparaffinised and the RNA can then be isolated. In comparison to low viscosity paraffin, however, pentadecane is more suitable since with pentadecane, after adding the lysis buffer and the proteolytic decomposition of the specimen, a clearer and sharper phase boundary between the organic and the aqueous phase is formed than when using low viscosity paraffin. The latter tends to form a dull intermediate phase in which parts of the specimen can possibly become caught.

EXAMPLE 5

Effect of the $K_{OW}$ Value of the Solvent Non-Miscible with Water Upon the Removal of Paraffin In the following experiments the dissolution of paraffin in various solvents non-miscible with water usable according to the invention are examined. For this purpose 82 mg paraffin are dissolved in 1640 µl chloroform so that for 1 mg paraffin there are 20 µl chloroform. From this aliquot parts of 200 µl, 100 µl, 50 µl and 25 µl are taken which correspond to 10, 5, 2.5 and 1.25 mg paraffin. These specimens are poured into Eppendorf specimen receptacles and the chloroform is evaporated at 60° C. Subsequently 1 ml respectively of the solvents specified below are added, the paraffin is dissolved by heating to 60° C., and then cooled down to 20° C., and the solubility of the paraffin in the solvent is assessed. The results are shown in the following Table I.

TABLE I

| Solubility of paraffin [mg] in 1 mL solvent at 20° C. | | | | | | | |
|---|---|---|---|---|---|---|---|
| | nonane | xylene | limonene | chloroform | penta-decane | sinarol | bio-diesel | Propionic acid pentyl ester |
| mg/ml | 50 | 50 | 50 | 50 | Approx. 40 | 33 | 25 | 10 |
| Kow value | 5.4 | 3.1 | 3.4 | 2 | 7.7 | Approx. 7 | Approx. 8 | 2.4 |
| | acetic acid butyl ester | decanol | octanoic acid | acetyl tributyl citrate | adipinic acid di-ethyl ester | malonic acid diethyl ester | benzyl alcohol |
| mg/ml | 5 | 5 | 5 | 2.5 | 1.25 | <1.25 | <1.25 |
| Kow value | 1.8 | 4.6 | 3.1 | 3.3 | 1.3 | 1 | 1.1 |

The specified $K_{OW}$ values are taken from the following sources or estimated from particular experiments:

BGIA—Institute for Safety at Work of the German Legal Accident Insurance GESTIS Materials Data Bank, LOGKOW—A database of evaluated octanol water partition coefficients (Log P)

PubChem Substance

These results show that the solubility of paraffins in the corresponding solvent non-miscible with water are generally greater the greater the Kow value of the latter is.

EXAMPLE 6

Effect of the $K_{OW}$ Value Upon the Phase Separation

In a further experiment the phase separation between the aqueous and organic phase was examined in relation to the aforementioned solvents. For this purpose 400 µl respectively of the respective organic solvent non-miscible with water was mixed with 1.25 mg/ml paraffin and 100 µl lysis buffer, followed by the addition of 100 µl 200 mM ammonium chloride. Next 200 µl ethanol (approximately 98%) are added and after mixing centrifuged in order to support the phase separation. In this way conditions comparable to the method according to the invention are created.

In order to evaluate the phase separation the volume of the aqueous phase was measured. The sum of the components, disregarding the volume concentration, is approximately 400 µl. Upon mixing with a solvent non-miscible with water, and which has a low $K_{OW}$ value of for example 1.0, a clearly larger volume of the aqueous phase of approximately 600 µl is produced, however. It follows from this that after adding ethanol, solvents with a low $K_{OW}$ value enable poorer separation of the aqueous phase from the organic phase. However, solvents with a $K_{OW}$ value of 4.0 or more provide a clearly better phase separation under the aforementioned conditions.

We claim:

1. A method for isolating biomolecules from a fixed biological specimen embedded in paraffin, comprising:
   bringing the biological specimen embedded in the paraffin into contact with a solvent immiscible with water and dissolving the paraffin in the solvent to form a liquid organic phase containing the biological specimen and the paraffin;
   bringing the liquid organic phase containing the biological specimen and the paraffin into contact with an aqueous phase containing an aqueous solution of at least one lysis substance and/or with water and at least one lysis substance such as to form a two-phase system of the liquid organic phase and the aqueous phase in contact with one another;
   wherein the biological specimen migrates from the liquid organic phase containing the paraffin to the aqueous phase while the liquid organic phase and the aqueous phase are in contact with one another;
   wherein the biological specimen is being lysed by the at least one lysis substance in the aqueous phase of the two-phase system, while the liquid organic phase and the aqueous phase are in contact with one another and the liquid organic phase contains the paraffin, to release the biomolecules from the biological specimen; and
   isolating the biomolecules from the aqueous phase while the liquid organic phase and the aqueous phase are in contact with one another and the liquid organic phase contains the paraffin.

2. The method according to claim 1, wherein the solvent immiscible with water is liquid at ≤20° C.

3. The method according to claim 1, wherein the solvent immiscible with water has a boiling point under normal pressure of at least 150° C.

4. The method according to claim 3, wherein the solvent immiscible with water has a flash point of at least 40° C.

5. The method according to claim 3, wherein the solvent immiscible with water has a flash point of at least 50° C.

6. The method according to claim 1, wherein the solvent immiscible with water has a boiling point under normal pressure of at least 160° C.

7. The method according to claim 1, wherein the solvent immiscible with water has a flash point of at least 40° C.

8. The method according to claim 1, wherein the solvent immiscible with water has a flash point of at least 50° C.

9. The method according to claim 1, wherein the solvent immiscible with water has a Kow value of at least 4.

10. The method according to claim 1, wherein the solvent immiscible with water has a Kow value of at least 5.

11. The method according to claim 1, wherein the release of the biomolecules from the biological specimen is conducted while the liquid organic phase and the aqueous phase are in contact with one another.

12. The method according to claim 1, wherein said forming of the two-phase system, said transferring, and said lysing are performed in a receptacle.

13. A method for isolating biomolecules from a fixed biological specimen embedded in paraffin, comprising:
bringing the biological specimen embedded in the paraffin into contact with a solvent immiscible with water and dissolving the paraffin in the solvent to form a liquid organic phase containing the biological specimen and the paraffin;
bringing the liquid organic phase containing the biological specimen and the paraffin into contact with an aqueous phase containing an aqueous solution of at least one lysis substance and/or with water and at least one lysis substance such as to form a two-phase system of the liquid organic phase and the aqueous phase in contact with one another;
wherein the biological specimen migrates from the liquid organic phase containing the paraffin to the aqueous phase while the liquid organic phase and the aqueous phase are in contact with one another;
wherein the biological specimen is being lysed by the at least one lysis substance in the aqueous phase of the two-phase system, while the liquid organic phase and the aqueous phase are in contact with one another and the liquid organic phase contains the paraffin, to release the biomolecules from the biological specimen; and
isolating the biomolecules from the aqueous phase while the liquid organic phase and the aqueous phase are in contact with one another and the liquid organic phase contains the paraffin,
wherein the solvent immiscible with water has a lesser density than water.

14. The method according to claim 13, wherein the solvent immiscible with water is liquid at ≤25° C.

15. The method according to claim 14, wherein the solvent immiscible with water has a boiling point under normal pressure of at least 150° C.

16. The method according to claim 15, wherein the solvent immiscible with water has a flash point of at least 40° C.

17. The method according to claim 15, wherein the solvent immiscible with water has a flash point of at least 50° C.

18. The method according to claim 14, wherein the solvent immiscible with water has a boiling point under normal pressure of at least 160° C.

19. The method according to claim 14, wherein the solvent immiscible with water has a flash point of at least 40° C.

20. The method according to claim 14, wherein the solvent immiscible with water has a flash point of at least 50° C.

21. The method according to claim 13, wherein the solvent immiscible with water is liquid at ≤20° C.

22. The method according to claim 13, wherein the solvent immiscible with water has a boiling point under normal pressure of at least 150° C.

23. The method according to claim 22, wherein the solvent immiscible with water has a flash point of at least 40° C.

24. The method according to claim 22, wherein the solvent immiscible with water has a flash point of at least 50° C.

25. The method according to claim 13, wherein the solvent immiscible with water has a boiling point under normal pressure of at least 160° C.

26. The method according to claim 13, wherein the solvent immiscible with water has a flash point of at least 40° C.

27. The method according to claim 13, wherein the solvent immiscible with water has a flash point of at least 50° C.

28. The method according to claim 13, wherein said forming of the two-phase system, said transferring, and said lysing are performed in a receptacle.

29. A method for isolating biomolecules from a fixed biological specimen embedded in paraffin, comprising:
bringing the biological specimen embedded in the paraffin into contact with a solvent immiscible with water and dissolving the paraffin in the solvent to form a liquid organic phase containing the biological specimen and the paraffin;
bringing the liquid organic phase containing the biological specimen and the paraffin into contact with an aqueous phase containing an aqueous solution of at least one lysis substance and/or with water and at least one lysis substance such as to form a two-phase system of the liquid organic phase and the aqueous phase in contact with one another;
wherein the biological specimen migrates from the liquid organic phase containing the paraffin to the aqueous phase while the liquid organic phase and the aqueous phase are in contact with one another;
wherein the biological specimen is being lysed by the at least one lysis substance in the aqueous phase of the two-phase system, while the liquid organic phase and the aqueous phase are in contact with one another and the liquid organic phase contains the paraffin, to release the biomolecules from the biological specimen; and
isolating the biomolecules from the aqueous phase while the liquid organic phase and the aqueous phase are in contact with one another and the liquid organic phase contains the paraffin,
wherein the solvent non-miscible with water is liquid at ≤25° C.

30. The method according to claim 29, wherein the solvent immiscible with water has a boiling point under normal pressure of at least 150° C.

31. The method according to claim 30, wherein the solvent immiscible with water has a flash point of at least 40° C.

32. The method according to claim 30, wherein the solvent immiscible with water has a flash point of at least 50° C.

33. The method according to claim 29, wherein the solvent immiscible with water has a boiling point under normal pressure of at least 160° C.

34. The method according to claim 29, wherein the solvent immiscible with water has a flash point of at least 40° C.

35. The method according to claim 29, wherein the solvent immiscible with water has a flash point of at least 50° C.

36. The method according to claim 29, wherein said forming of the two-phase system, said transferring, and said lysing are performed in a receptacle.

* * * * *

UNITED STATES PATENT AND TRADEMARK OFFICE
CERTIFICATE OF CORRECTION

PATENT NO. : 9,845,488 B2
APPLICATION NO. : 12/827210
DATED : December 19, 2017
INVENTOR(S) : Kirsch et al.

Page 1 of 1

It is certified that error appears in the above-identified patent and that said Letters Patent is hereby corrected as shown below:

On the Title Page

Item (75) Inventor is corrected to read:
-- Christoph Kirsch, Pulheim (DE);
Claudia Beyard, Zuelpich (DE);
Markus Meusel, Wuerselen (DE) --.

Signed and Sealed this
Sixth Day of November, 2018

Andrei Iancu
*Director of the United States Patent and Trademark Office*